US011466312B2

(12) United States Patent
Park et al.

(10) Patent No.: US 11,466,312 B2
(45) Date of Patent: Oct. 11, 2022

(54) METHOD FOR DETECTING TARGET RNA BY UTILIZING NICKING/EXTENSION CHAIN REACTION SYSTEM-BASED ISOTHERMAL NUCLEIC ACID AMPLIFICATION

(71) Applicants: KOREA ADVANCED INSTITUTE OF SCIENCE AND TECHNOLOGY, Daejeon (KR); BIONANO HEALTH GUARD RESEARCH CENTER, Daejeon (KR)

(72) Inventors: Hyun Gyu Park, Daejeon (KR); Hyo Yong Kim, Daejeon (KR); Yong Ju, Daejeon (KR); Jun Ki Ahn, Daejeon (KR)

(73) Assignees: KOREA ADVANCED INSTITUTE OF SCIENCE AND TECHNOLOGY, Daejeon (KR); BIONANO HEALTH GUARD RESEARCH CENTER, Daejeon (KR)

(*) Notice: Subject to any disclaimer, the term of this patent is extended or adjusted under 35 U.S.C. 154(b) by 129 days.

(21) Appl. No.: 16/958,683

(22) PCT Filed: Dec. 31, 2018

(86) PCT No.: PCT/KR2018/016946
§ 371 (c)(1),
(2) Date: Jun. 27, 2020

(87) PCT Pub. No.: WO2019/132626
PCT Pub. Date: Jul. 4, 2019

(65) Prior Publication Data
US 2021/0363566 A1 Nov. 25, 2021

(30) Foreign Application Priority Data
Dec. 29, 2017 (KR) .................. 10-2017-0183675

(51) Int. Cl.
*C12Q 1/683* (2018.01)
(52) U.S. Cl.
CPC ...... *C12Q 1/683* (2013.01); *C12Y 207/07049* (2013.01)
(58) Field of Classification Search
CPC .......... C12Q 1/6865; C12Q 2537/1376; C12Q 2521/101; C12Q 2521/107;
(Continued)

(56) References Cited

U.S. PATENT DOCUMENTS

2009/0092967 A1* 4/2009 Yao ................. C12Q 1/6806
435/6.12
2013/0040840 A1* 2/2013 Huang .............. C12Q 1/6804
506/9

FOREIGN PATENT DOCUMENTS

KR 1020120055224 A 5/2012
KR 1020130094498 A 8/2013
(Continued)

OTHER PUBLICATIONS

Walker et al., "Strand displacement amplification—an isothermal, in vitro DNA amplification technique," Nucleic Acids Research, vol. 20, No. 7, pp. 1691-1696. (Year: 1992).*
(Continued)

*Primary Examiner* — Young J Kim
(74) *Attorney, Agent, or Firm* — Hultquist, PLLC; Steven J. Hultquist (57) ABSTRACT

The present invention relates to a detection method for detecting a target RNA contained in a sample with high sensitivity by using nicking/extension chain reaction system-based isothermal nucleic acid amplification (NESBA) that uses activity of a cleavage enzyme and a DNA polymerase. The NESBA of the present invention is a new concept isothermal target RNA detection method that real-
(Continued)

izes higher amplification efficiency than the existing NASBA technology and is deemed to be utilizable as a new concept diagnosis technology that can replace conventional target RNA detection technologies.

5 Claims, 4 Drawing Sheets

Specification includes a Sequence Listing.

(58) Field of Classification Search
CPC ........ C12Q 2525/131; C12Q 2531/101; C12Q 1/68; C12Y 207/07049
See application file for complete search history.

(56) References Cited

FOREIGN PATENT DOCUMENTS

| KR | 1020160108377 A | 9/2016 |
| KR | 1020170067242 A | 6/2017 |

OTHER PUBLICATIONS

Phillips et al., "Antisense RNA Amplification: A Linear Amplification Method for Analyzing the mRNA Population from Single Living Cells," Methods: A Companion to Methods in Enzymology, vol. 10, pp. 283-288. (Year: 1996).*

Anderson, M., Ed., "Nucleic Acid Hybridization", "Nucleic Acid Hybridization", 1999, Page(s) Abstract, Publisher: Bios Scientific Publishers Ltd.

Sambrook, J., et al., "Molecular Cloning: A Laboratory Manual, 3rd Edition", 2001, Page(s) (Abstract Only), Publisher: Cold Spring Harbor Laboratory Press.

Gill, P., et al., "Nucleic Acid Isothermal Amplification Technologies—A Review", "Nucleosides, Nucleotides and Nucleic Acids", 2008, pp. 224-243, vol. 27, No. 3.

Kievits, T., et al., "NASBA Isothermal Enzymatic In Vitro Nucleic Acid Amplification Optimized for the Diagnosis of HIV-1 Infection", "Journal of Virological Materials", 1991, pp. 273-286, vol. 35.

Maxam, A., et al., "Sequencing End-Labeled DNA with Base-Specific Chemical Cleavages", "Methods in Enzymology", 1980, pp. 499-561, vol. 65.

* cited by examiner

SEQUENCE LISTING

```
<160> NUMBER OF SEQ ID NOS: 3

<210> SEQ ID NO 1
<211> LENGTH: 59
<212> TYPE: DNA
<213> ORGANISM: Artificial Sequence
<220> FEATURE:
<223> OTHER INFORMATION: primer

<400> SEQUENCE: 1
aaaaaaagga tcggggaatt ctaatacgac tcactatagg ggatgcttga gcatacagg      59

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
aaaaaaagga tcggggagct ctgcttgcat aag                                  33
```

```
<210> SEQ ID NO 3
<211> LENGTH: 25
<212> TYPE: DNA
<213> ORGANISM: Artificial Sequence
<220> FEATURE:
<223> OTHER INFORMATION: molecular beacon

<400> SEQUENCE: 3
ccagcattga acgtgactat gctgg                                                 25
```

METHOD FOR DETECTING TARGET RNA BY UTILIZING NICKING/EXTENSION CHAIN REACTION SYSTEM-BASED ISOTHERMAL NUCLEIC ACID AMPLIFICATION

CROSS-REFERENCE TO RELATED APPLICATIONS

This application is a U.S. national phase under the provisions of 35 U.S.C. § 371 of International Patent Application No. PCT/KR18/16946 filed Dec. 31, 2018, which in turn claims priority under 35 U.S.C. § 119 of Korean Patent Application No. 10-2017-0183675 filed Dec. 29, 2017. The disclosures of International Patent Application No. PCT/KR18/16946 and Korean Patent Application No. 10-2017-0183675 are hereby incorporated herein by reference in their respective entireties, for all purposes.

TECHNICAL FIELD

The present invention relates to a method of amplifying and detecting a target RNA, and more particularly to a method of amplifying and detecting a target RNA using nicking/extension-chain-reaction-system-based isothermal nucleic acid amplification (NESBA).

BACKGROUND ART

As living quality has improved, modern people's interest in early diagnosis of disease has grown, and such interest has a direct influence on the growth of the diagnosis market. According to the Frost & Sullivan survey, the global in-vitro diagnosis market recorded an annual growth rate (CAGR) of 7.3%, starting at about 47 billion dollars in 2013 and reaching a scale of about 63 billion dollars in 2017. In addition, among various technical fields in the rapidly growing in-vitro diagnosis market, molecular diagnostic and on-site diagnostic fields have been observed to be the technical fields recording the highest growth rates, namely 12.7% and 8.4%, respectively. Molecular diagnostic technology enables the direct detection of genetic information (DNA/RNA) of a pathogen that causes a disease, and thus is receiving much attention as a technology capable of addressing disadvantages of immunodiagnostic technology for detecting indirect factors of a disease on the basis of known antigen/antibody reactions. In addition, on-site diagnostic technology is a technology that can remarkably reduce the time and expense associated with use of large hospitals or specialized diagnostic centers for checkups, unlike conventional diagnostic technologies.

With the rapid advance in these molecular diagnostic and on-site diagnostic technical fields, the severity of disease-related problems caused by RNA viruses has recently emerged. An example that can show the severity of RNA virus diseases is the 2015 Middle East Respiratory Syndrome (MERS). MERS is a viral respiratory infection caused by coronavirus (a type of RNA virus), and in 2015, 1,599 cases of MERS infections occurred worldwide, and a fatality rate of about 40% was recorded (as of Jun. 26, 2015). In the same year in Korea, 186 MERS cases occurred as of July 5, starting with the first confirmed patient on May 20, and 38 deaths occurred by November. As such, in the case of diseases caused by RNA viruses, great human damage easily occurs, and this can be said to result from a high mutation rate, which is a characteristic of RNA viruses. Due to this characteristic of RNA viruses, it is difficult to diagnose whether or not an infection occurs, and as a result, it is difficult to diagnose and deal with a disease early.

Technology has been developed to address these problems, and among various technologies that have been developed to date, the most representative diagnostic technology used in RNA virus detection is a reverse transcription polymerase chain reaction (RT-PCR). RT-PCR is a technique of generating complementary DNA (cDNA) from target RNA using a reverse transcriptase before a DNA amplification reaction and then amplifying the produced complementary DNA through PCR. This technique is advantageous in that a target DNA can be detected with high sensitivity using the high amplification efficiency of PCR, and is a technique that has been essentially used to confirm a disease to date. However, in order to implement such a RT-PCR technique, sophisticated temperature control for a nucleic acid amplification reaction is required, which acts as a factor that hinders the miniaturization of diagnostic devices. Therefore, the RT-PCR technique is disadvantageous in that it can be used only in limited facilities such as large hospitals or specialized diagnostic centers equipped with diagnostic equipment.

As an RNA detection technique capable of addressing the disadvantage of the aforementioned RT-PCR technique, nucleic-acid-sequence-based amplification (hereinafter referred to as NASBA) was developed (Kievits et al., Journal of Virological Methods, 35:273, 1991). NASBA involves amplification and detection reactions of target RNA under isothermal conditions (41° C.), and thus has been used as a new isothermal nucleic acid amplification technique capable of addressing the problems of existing RT-PCR. NASBA is based on a reaction in which a T7-promoter-containing double-stranded DNA is produced from target RNA, and then a large amount of anti-sense RNA is produced through a T7 RNA polymerase transcription reaction. In addition, the produced anti-sense RNA can be used as a substrate for the production reaction of a T7-promoter-containing double-stranded DNA, thereby implementing an amplification reaction with high efficiency. However, NASBA is disadvantageous in that the anti-sense RNA amplification reaction is dependent only on the transcription reaction of T7 RNA polymerase. Thus, when the efficiency of the reaction in which a T7-promoter-containing double-stranded DNA is produced from target RNA is low, a problem may also occur in the efficiency of the anti-sense RNA amplification reaction based on the transcription reaction of T7 RNA polymerase, which may act as a factor that generates a false signal.

Therefore, as a result of having made intensive efforts to address the above-described problems with the related art, the inventors of the present invention confirmed that, by introducing a primer modified with an nicking enzyme recognition nucleotide sequence into existing NASBA, the exponential amplification reaction of a T7-promoter-containing double-stranded DNA was performed on the basis of nicking enzyme and DNA polymerase activity, and then an anti-sense RNA was produced, and as a result, a new concept isothermal nucleic acid amplification reaction with high amplification efficiency compared to the existing NASBA can be implemented, and thus completed the present invention.

DISCLOSURE

Technical Problem

Therefore, the present invention has been made in view of the above problems, and it is an object of the present invention to provide a method of increasing target RNA detection sensitivity by enhancing the nucleic acid amplification reaction efficiency of existing NASBA through nicking/extension-chain-reaction-system-based isothermal nucleic acid amplification.

Technical Solution

In accordance with an aspect of the present invention, the above and other objects can be accomplished by the provision of a method of detecting of a target RNA based on a nicking/extension chain reaction system, comprising:

(a) hybridizing a target RNA with a first primer including a sequence complementary to the target RNA, a T7 promoter sequence, and a DNA nicking enzyme recognition nucleotide sequence, and then producing complementary DNA of the target RNA using a reverse transcriptase;

(b) degrading the target RNA bound to the complementary DNA produced in step (a) by a ribonuclease;

(c) hybridizing the complementary DNA with a second primer including a sequence complementary to the complementary DNA and a DNA nicking enzyme recognition nucleotide sequence, and then producing a double-stranded DNA including a T7 promoter and the nicking enzyme recognition nucleotide sequence using a reverse transcriptase;

(d) treating the double-stranded DNA produced in step (c) with a DNA endonuclease to cleave a DNA nicking enzyme recognition site of the double-stranded DNA, and then amplifying the T7-promoter-containing double-stranded DNA using DNA polymerase; and (e) producing an anti-sense RNA from the T7-promoter-containing double-stranded DNA amplified in step (d) using T7 RNA polymerase, and then detecting the produced anti-sense RNA.

In accordance with another aspect of the present invention, there is provided a composition for detecting a target RNA, comprising: (i) a first primer comprising a sequence complementary to the target RNA, a T7 promoter sequence, and a DNA nicking enzyme recognition nucleotide sequence; and (ii) a second primer comprising a sequence complementary to DNA complementary to the target nucleic acid and a DNA nicking enzyme recognition nucleotide sequence.

In accordance with a further aspect of the present invention, there is provided a kit for detecting a target RNA, comprising: (i) a first primer comprising a sequence complementary to the target RNA, a T7 promoter sequence, and a DNA nicking enzyme recognition nucleotide sequence; and (ii) a second primer including a sequence complementary to DNA complementary to the target nucleic acid and a DNA nicking enzyme recognition nucleotide sequence.

DESCRIPTION OF DRAWINGS

The above and other objects, features and other advantages of the present invention will be more clearly understood from the following detailed description taken in conjunction with the accompanying drawings, in which:

FIG. 1 illustrates a NESBA reaction of the present invention, wherein FIG. 1(A) illustrates a reaction in which a T7-promoter-containing double-stranded DNA is produced from a target RNA, FIG. 1(B) illustrates a reaction in which the T7-promoter-containing double-stranded DNA produced as illustrated in FIG. 1(A) is exponentially amplified through a nicking/polymerase chain reaction, and FIG. 1(C) illustrates a reaction in which an anti-sense RNA is produced from the T7-promoter-containing double-stranded DNA produced as illustrated in FIG. 1(B) through the activity of T7 RNA polymerase;

DETAILED DESCRIPTION AND EXEMPLARY EMBODIMENTS

Reference will now be made in detail to the preferred embodiments of the present invention, examples of which are illustrated in the accompanying drawings. Wherever possible, the same reference numbers will be used throughout the drawings to refer to the same or like parts.

Unless defined otherwise, all technical and scientific terms used herein have the same meanings as commonly understood by one of ordinary skill in the art to which the present invention pertains. In general, the nomenclature used herein and experimental methods described below are well known and commonly used in the art.

In the present invention, to develop a method of amplifying a final RNA product (hereinafter referred to as an anti-sense RNA) produced when a target RNA is present through T7 RNA polymerase activity at isothermal temperature and of detecting the amplified anti-sense RNA, without using expensive analysis equipment for precisely performing temperature changes, by introducing nicking/extension-chain-reaction-system-based isothermal nucleic acid amplification, a T7-promoter-containing double-stranded DNA, which is produced in an existing NASBA technique, was exponentially amplified, and therefore a method of enhancing the production efficiency of an anti-sense RNA was developed.

Therefore, the present invention relates to a method of detecting a target RNA on the basis of a nicking/extension chain reaction system, the method comprising: (a) hybridizing a target RNA with a first primer comprising a sequence complementary to the target RNA, a T7 promoter sequence, and a DNA nicking enzyme recognition nucleotide sequence, and then producing complementary DNA of the target RNA using a reverse transcriptase; (b) degrading the target RNA bound to the complementary DNA produced in step (a) by a ribonuclease; (c) hybridizing the complementary DNA with a second primer comprising a sequence complementary to the complementary DNA and a DNA nicking enzyme recognition nucleotide sequence, and then producing a double-stranded DNA comprising a T7 promoter and the nicking enzyme recognition nucleotide sequence using a reverse transcriptase; (d) treating the double-stranded DNA produced in step (c) with a DNA nicking enzyme to cleave a DNA nicking enzyme recognition site of the double-stranded DNA, and then amplifying the T7-promoter-containing double-stranded DNA using DNA polymerase; and (e) producing an anti-sense RNA from the T7-promoter-containing double-stranded DNA amplified in step (d) using T7 RNA polymerase, and then detecting the produced anti-sense RNA. (see FIG. 1).

In step (a) of the present invention, the target RNA binds to and is hybridized with a sequence complementary to the target RNA of the first primer (sequence complementary to target RNA+T7 promoter sequence+DNA nicking enzyme recognition site sequence), a reverse transcriptase binds to the first primer that is hybridized with the target RNA to produce DNA complementary to the target RNA, and the target RNA and DNA complementary thereto complementarily bind to each other.

In step (b) of the present invention, the target RNA bound to the complementary DNA produced in step (a) is degraded with a ribonuclease, and consequently, a DNA strand, including the sequence complementary to the target RNA, a T7 promoter, and the nicking enzyme recognition nucleotide sequence, remains.

In step (c) of the present invention, the DNA strand including the sequence complementary to the target RNA, a T7 promoter, and the nicking enzyme recognition nucleotide sequence, which remains in step (b), binds to and is hybridized with a second primer (sequence complementary to the DNA strand+nicking enzyme recognition sequence), a reverse transcriptase binds to the hybridized primer to synthesize a complementary DNA strand, and consequently, a double-stranded DNA including the sequence complementary to the target RNA, the T7 promoter sequence, and the nicking enzyme recognition sequence is produced.

In step (d) of the present invention, the double-stranded DNA produced in step (c) (a sequence complementary to the target RNA+a T7 promoter sequence+an nicking enzyme recognition sequence) is treated with a DNA nicking enzyme that recognizes and cleaves the nicking enzyme recognition sequence, thereby cleaving a single strand of the double-stranded DNA. The cleaved DNA strand is used as a primer for new DNA synthesis to synthesize a new DNA strand using DNA polymerase present in a sample, and the previously bound DNA strand is released by the strand displacement activity of the DNA polymerase. The released DNA strand binds to and is hybridized with a first primer or a second primer that has not participated in the reaction, is synthesized by DNA polymerase into a double-stranded DNA, and is cleaved by a DNA nicking enzyme, and the DNA polymerase binds to the cleaved strand, thereby synthesizing a new DNA strand, and the previously bound DNA strand is released, and these processes are repeated, through which a double-stranded DNA including a sequence complementary to the target RNA and a T7 promoter is exponentially amplified.

In step (e) of the present invention, T7 RNA polymerase is used to produce an anti-sense RNA from the double-stranded DNA including the sequence complementary to the target RNA and a T7 promoter, which has been amplified in step (d), and the produced anti-sense RNA is detected.

In the present invention, steps (a) to (e) may be performed at isothermal temperature, preferably at a temperature ranging from 40° C. to 42° C.

In the present invention, the "first primer" has a sequence including a sequence complementary to a target RNA, a T7 promoter sequence, and a DNA nicking enzyme recognition nucleotide sequence, and in step (a), the sequence complementary to the target RNA of the first primer and the target RNA bind to and are hybridized with each other, and a reverse transcriptase binds to the first primer hybridized with the target RNA, and consequently, DNA complementary to the target RNA is produced from the target RNA. In addition, in step (d), the DNA strand released by the action of the DNA polymerase binds to and is hybridized with a first primer or a second primer that has not participated in the reaction, and is synthesized by DNA polymerase into a double-stranded DNA.

In one embodiment of the present invention, for example, a primer of SEQ ID NO: 1 below is used as the first primer, wherein the italic portion (GG ATC) denotes a DNA nicking enzyme recognition site, the underlined bold portion denotes a T7 promoter site (TAA TAC GAC TCA CTA TAG), and the "GGG ATG CTT GAG CAT ACA GG" site is a site complementary to the target RNA.

First primer: 5'-AAA AAA AGG ATC GGG GAA TTC TAATACGACTCACTATAG GGG ATG CTT GAG CAT ACA GG (SEQ ID NO: 1)

In the present invention, the above sequence is used as an example, but the sequence of used primer varies depending on the types of target RNA and DNA nicking enzyme.

In the present invention, the "second primer" has a sequence including a sequence complementary to DNA complementary to the target RNA and an nicking enzyme recognition nucleotide sequence, and in step (c), the second primer binds to and is hybridized with the remaining "DNA strand including the sequence complementary to the target RNA, a T7 promoter, and the nicking enzyme recognition nucleotide sequence," a reverse transcriptase binds to the hybridized primer to synthesize a complementary DNA strand, and consequently, a double-stranded DNA including the sequence complementary to the target RNA, a T7 promoter sequence, and the nicking enzyme recognition sequence is produced. In addition, in step (d), the DNA strand released by the action of the DNA polymerase binds to and is hybridized with a first primer or a second primer that has not participated in the reaction, and is synthesized by the DNA polymerase into a double-stranded DNA.

In one embodiment of the present invention, for example, a primer of SEQ ID NO: 2 below is used as the second primer, wherein the italic portion (GG ATC) denotes a DNA nicking enzyme recognition sequence, and the underlined portion (GGG GAG CTC TGC TTG CAT AAG G) denotes a sequence complementary to DNA complementary to the target RNA.

Second primer: 5'-AAA AAA AGG ATC GGGGAGCTCTGCTTGCATAAGG-3'(SEQ ID NO: 2) In the present invention, the above sequence is used as an example, but the sequence of used primer varies depending on the types of target RNA and DNA endonuclease.

In the present invention, the ribonuclease is not limited, as long as it is an enzyme that selectively degrades only RNA in a DNA/RNA hybrid, and may be RNaseH, RNaseT1, or the like, but preferably, RNaseH or the like may be used.

In the present invention, the DNA polymerase is not limited, as long as it is a DNA polymerase having strand displacement activity on DNA bound to a template, and preferably, a Klenow fragment or the like may be used.

Examples of various DNA polymerases that may be used in the present invention include a Klenow fragment of *E. coli* DNA polymerase I, a thermostable DNA polymerase, and a bacteriophage T7 DNA polymerase. Preferably, the polymerase is a thermostable DNA polymerase that can be obtained from various bacteria species, and examples thereof include *Thermus aquaticus* (Taq), *Thermus thermophilus* (Tth), *Thermus filiformis, Thermus flavus, Thermococcus litoralis,* and *Pyrococcus furiosus* (Pfu). When a polymerization reaction is performed, components required for the reaction may be provided in excess amounts in a reaction container. Excess amounts of components required for an amplification reaction refer to amounts such that the amplification reaction is not substantially limited by the concentrations of the components.

In the present invention, the DNA nicking enzyme may be a nicking endonuclease, and is not limited, as long as it is an enzyme that recognizes and cleaves the specific recognition site of a DNA nucleotide sequence. The nicking endonuclease is an enzyme that catalyzes recognition of the specific nucleotide sequence of a double-stranded DNA molecule and cleavage of a portion thereof or the periphery thereof, and most nicking endonucleases cleave DNA at a location with a specific nucleotide sequence, which is referred to as a recognition site or a restriction site.

The site recognized by a nicking endonuclease has a specific sequence called a palindrome. That is, this means that the recognition site has the same nucleotide sequence in the 5' to 3' direction of both strands. The specific nucleotide sequence denotes a recognition site. For example, the enzyme EcoRI cleaves DNA only when it meets the nucleotide sequence of GAATTC in a DNA double helix to form a 5'-overhanging sticky end. In the present invention, the nicking endonuclease is not limited, as long as it is an enzyme that recognizes and cleaves the specific recognition site of a DNA nucleotide sequence, and may be, for example, EcoRI, BamHI, HindIII, KpnI, NotI, PstI, SmaI, XhoI, or the like.

In the present invention, "anti-sense" refers to an oligomer with a sequence of nucleotide bases and a backbone between sub-units that allow the anti-sense oligomer to hybridize with a target sequence in RNA by Watson-Crick base pairing, to form a RNA:oligomer heteroduplex within the target sequence, typically with mRNA. The oligomer may have exact sequence complementarity to the target sequence or near complementarity.

It is required to add co-factors such as $Mg^{2+}$, dATP, dCTP, dGTP, and dTTP to a reaction mixture to the extent to which a desired amplification degree can be achieved. All enzymes used in the amplification reaction may be active under the same reaction conditions. In fact, buffers provide conditions close to an optimum reaction conditions for all enzymes. Thus, the amplification process of the present invention may be carried out on a single reactant without changing conditions such as adding reactants.

According to one embodiment of the present invention, a molecular beacon including a sequence complementary to the target RNA is used as a means for detecting an anti-sense RNA. In addition, various types of probes that bind to the target nucleic acid may be used, and the term "probe" as used herein refers to a single-strand nucleic acid molecule which includes a sequence complementary to a target nucleic acid sequence. According to one embodiment of the present invention, the probes of the present invention may be modified within the scope that does not impair the advantages of the probes of the present invention, i.e., improvement in hybridization specificity. These modifications, i.e., labels, may provide a signal to detect the presence or absence of hybridization, and may be linked to oligonucleotides. Suitable labels include fluorophores (e.g., fluorescein, phycoerythrin, rhodamine, lissamine, and Cy3 and Cy5 (Pharmacia)), chromophores, chemi-luminophores, magnetic particles, radioisotopes ($P^{32}$ and $S^{35}$), mass labeling, electron dense particles, enzymes (alkaline phosphatase or horseradish peroxidase), cofactors, substrates for enzymes, heavy metals (e.g., gold) and hapten, with specific binding partners such as antibodies, streptavidin, biotin, digoxigenin and chelating groups, but the present invention is not limited thereto. Labeling may be performed using various methods commonly used in the art, for example, a nick translation method, a random priming method (Multiprime DNA labelling systems booklet, "Amersham" (1989)), and a Kination method (Maxam & Gilbert, Methods in Enzymology, 65:499 (1986)). Labels provide signals detectable using fluorescence, radioactivity, colorimetry, gravimetric measurement, X-ray diffraction or absorption, magnetism, enzymatic activity, mass analysis, binding affinity, hybridization high frequency, and nanocrystals.

According to one embodiment of the present invention, a probe may be used as a means for detecting an anti-sense RNA, and the probe of the present invention may be immobilized on a water-insoluble carrier (e.g., a nitrocellulose or nylon filter, a glass plate, a silicone and a fluorocarbon support) to be manufactured as a microarray. In the microarray, the probe of the present invention is used as a hybridizable array element. The immobilization onto the water-insoluble carrier is performed by a chemical bonding method or a covalent bonding method such as UV. For example, the hybridizable array element may bind to a glass surface modified so as to include an epoxy compound or an aldehyde group, and may also bind to a polylysine coating surface by UV. In addition, the hybridizable array element may bind to a carrier via a linker (e.g., an ethylene glycol oligomer and a diamine). When the probe is used, the probe is hybridized with an anti-sense RNA molecule. In the present invention, suitable hybridization conditions may be determined through a series of processes by an optimized procedure. For example, conditions such as temperature, the concentration of components, hybridization and washing time, buffer components, and pH and ionic strength thereof depend on various factors such as the length of a probe, GC content, a target nucleotide sequence, and the like. The detailed conditions for hybridization can be confirmed in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999). After the hybridization reaction, a hybridization signal generated through the hybridization reaction is detected. Detection of hybridization signaling may be performed using various methods, for example, depending on the type of label bound to the probe. For example, when the probe is labeled with an enzyme, a substrate of the enzyme may be reacted with a hybridization reaction product to confirm the presence or absence of hybridization. Suitable combinations of enzyme/substrate include a peroxidase (e.g., horseradish peroxidase) and chloronaphthol, aminoethylcarbazole, diaminobenzidine, D-luciferin, bis-N-methylacridinium nitrate (lucigenin), resorufin benzyl ether, luminol, an Amplex red reagent (10-acetyl-3,7-dihydroxyphenoxazine), p-phenylenediamine-HCl and pyrocatechol (HYR), tetramethylbenzidine (TMB), 2,2'-azine-di[3-ethylbenzthiazoline sulfonate] (ABTS), o-phenylene diamine (OPD), and naphthol/pyronine; alkaline phosphatase and bromochloroindolyl phosphate (BCIP), nitroblue tetrazolium (NBT), naphthol-AS-B1-phosphate and ECF substrate; glucose oxidase and nitroblue tetrazolium (t-NBT); and the like. When the probe is labeled with gold particles, this may be detected by a silver staining method using silver nitrate. By analyzing the intensity of the hybridizable signal through the above-described hybridization process, the target RNA may be detected.

In the NESBA of the present invention, unlike the existing NASBA, primers including DNA nicking enzyme recognition nucleotide sequences are used to produce a double-stranded DNA including a T7 promoter and the DNA nicking enzyme recognition nucleotide sequence. A single strand of the double-stranded DNA is cleaved by the activity of a nicking enzyme recognizing the nicking enzyme recognition nucleotide sequence present in a sample. A short DNA strand produced by the cleavage reaction is used as a primer for new DNA synthesis, and thus a new DNA synthesis reaction proceeds based on the activity of DNA polymerase present in the sample. The DNA polymerase used in this reaction has strand displacement activity on DNA bound to a template in the DNA synthesis reaction. Thus, when new DNA is synthesized using the produced short DNA strand as a primer, the DNA bound to a template is released, and this DNA released from the template may be used as a template to which a primer that has not participated in the reaction can bind. Accordingly, the nicking/extension chain reaction is implemented through the nicking enzyme and DNA polymerase activity, thereby exponentially amplifying a T7-promoter-containing double-stranded DNA, which may be a core factor that can realize enhanced amplification efficiency compared with existing NASBA reactions.

Figure 1:
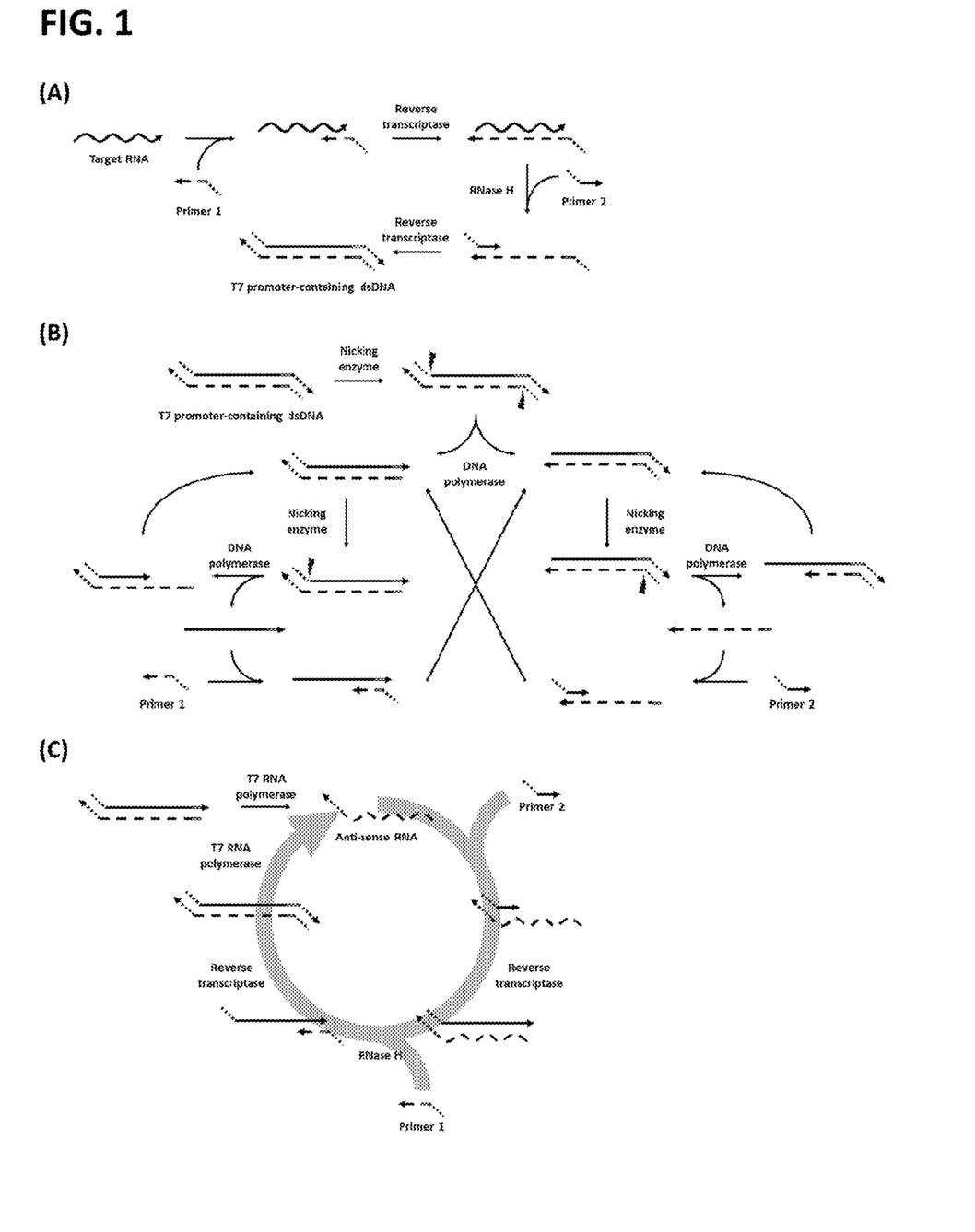

FIG. 1 illustrates a NESBA technique of the present invention, wherein FIG. 1(A) illustrates a reaction in which a T7-promoter-containing double-stranded DNA is produced from a target RNA, FIG. 1(B) illustrates a reaction in which the T7-promoter-containing double-stranded DNA produced as illustrated in FIG. 1(A) is exponentially amplified through a nicking/polymerase chain reaction, and FIG. 1(C) illustrates a reaction in which an anti-sense RNA is produced from the T7-promoter-containing double-stranded DNA produced as illustrated in FIG. 1(B) through the activity of T7 RNA polymerase.

Figure 2:
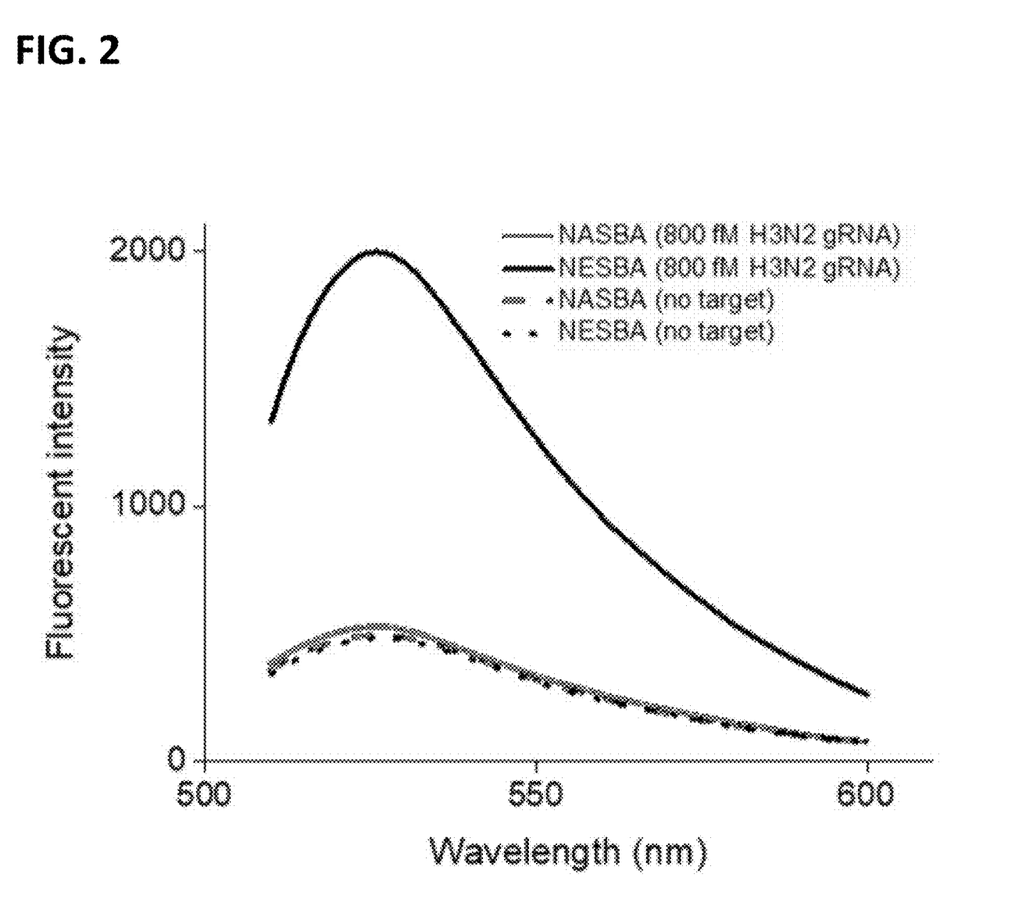
FIG. 2 illustrates the results of comparing the amplification efficiency of NESBA of the present invention with that of existing NASBA.

In one embodiment of the present invention, as a result of experimentally examining whether or not amplification efficiency of the NESBA technique of the present invention is enhanced, it was confirmed that the present invention showed a much higher amplification efficiency in an experiment for detecting a target RNA at the same concentration (H3N2 influenza gRNA, 800 fM) compared to existing NASBA reactions (see FIG. 2).

In addition, in another embodiment of the present invention, it was confirmed that the limit of detection (LOD) of target RNA for the NESBA technique of the present invention was 0.72 fM, from which it was confirmed that the NESBA technique has very high detection sensitivity. These results mean that the NESBA technique of the present invention has detection sensitivity similar to that of an existing reverse transcription PCR technique, under isothermal conditions without expensive analysis devices.

Another embodiment of the present invention relates to a composition for detecting a target RNA, comprising: (i) a first primer comprising a sequence complementary to the target RNA, a T7 promoter sequence, and a DNA nicking enzyme recognition nucleotide sequence; and (ii) a second primer comprising a sequence complementary to DNA complementary to the target nucleic acid and a DNA nicking enzyme recognition nucleotide sequence.

In the present invention, the composition for detecting a target RNA may further comprise a reverse transcriptase, T7 RNA polymerase, a DNA nicking enzyme, DNA polymerase, and dNTP.

Another embodiment of the present invention relates to a kit for detecting a target RNA, comprising: (i) a first primer comprising a sequence complementary to the target RNA, a T7 promoter sequence, and a DNA nicking enzyme recognition nucleotide sequence; and (ii) a second primer comprising a sequence complementary to DNA complementary to the target nucleic acid and a DNA nicking enzyme recognition nucleotide sequence.

In the present invention, the kit for detecting a target RNA may further comprising a reverse transcriptase, T7 RNA polymerase, a DNA nicking enzyme, DNA polymerase, and dNTP.

Hereinafter, the present invention will be described in further detail with reference to the following examples. It will be obvious to those of ordinary skill in the art that these examples are provided for illustrative purposes only and should not be construed as limiting the scope of the present invention.

Example 1. Establishment of Nicking/Extension-Chain-Reaction-System-Based Isothermal Nucleic Acid Amplification Reaction Conditions Using Nicking Enzyme and DNA Polymerase Activity A NESBA reaction solution used in the present example was prepared by adding, to a reaction buffer solution, 2.8 µL of rNTPs (25 mM each), 1.4 µL of dNTPs (10 mM each), 0.5 µL of a first primer (10 µM), 0.5 µL of a second primer (10 µM), 1 µL of a molecular beacon (6 µM), and 0.4 µL of a target RNA (H3N2 influenza virus gRNA), and the reaction buffer solution includes 40.4 mM Tris-HCl (pH 8.2), 50 mM NaCl, 53.2 mM KCl, 19.1 mM $MgCl_2$, 7.7 mM DTT, 11.4% DMSO, and 90 µg/mL BSA. The reaction solution was heated at 65° C. for 5 minutes, and then slowly cooled to 41° C. at a rate of 0.1° C./s and allowed to stand for 5 minutes. Subsequently, 5 µL of a NASBA enzyme cocktail (AMV-RT, RNase H, T7 RNA polymerase), 1.6 µL of a Klenow fragment (3'5' exo-) (5 unit/µL), and 0.5 µL of Nt.AlwI (10 unit/µL) were added to the reaction solution, and then a reaction was allowed to occur at 41° C. for 2 hours. After the reaction was completed, a fluorescence signal generated from a fluorescein (FAM) modified in the molecular beacon was measured to analyze the amount of anti-sense RNA that was produced.

The nucleotide sequence information used in the present example is as follows, but the present invention is not limited thereto.

```
First primer:
                                    (SEQ ID NO: 1)
5'-AAA AAA AGG ATC GGG GAA TTC TAA TAC GAC TCA
CTA TAG GGG ATG CTT GAG CAT ACA GG-3'

Second primer:
                                    (SEQ ID NO: 2)
5'-AAA AAA AGG ATC GGG GAG CTC TGC TTG CAT AAG

G-3'

Molecular beacon:
                                    (SEQ ID NO: 3)
5'-[FAM] CCA GCA TTG AAC GTG ACT ATG CTG G

[DABCYL]-3'
```

In addition, an anti-sense RNA was produced from the target RNA using a conventional technique, NASBA, as a control. More specifically, a NASBA reaction solution was prepared by adding, to a reaction buffer solution, 2.8 µL of rNTPs (25 mM each), 1.4 µL of dNTPs (10 mM each), 0.5 µL of a first primer (10 µM), 0.5 µL of a second primer (10 µM), 1 µL of a molecular beacon (6 µM), and 0.4 µL of a target RNA (H3N2 influenza virus gRNA), and the reaction buffer solution includes 40 mM Tris-HCl (pH 8.5), 12 mM $MgCl_2$, 70 mM KCl, 10 mM DTT, and 15% DMSO. In addition, the first and second primers used in the present NASBA reaction do not include an nicking enzyme recognition nucleotide sequence. The reaction solution was heated at 65° C. for 5 minutes and then slowly cooled to 41° C. at a rate of 0.1° C./s, and allowed to stand for 5 minutes.

Subsequently, 5 μL of a NASBA enzyme cocktail (AMV-RT, RNase H, T7 RNA polymerase) was added to the reaction solution, and then a reaction was allowed to occur at 41° C. for 2 hours. After the reaction was completed, a fluorescence signal generated from a fluorescein (FAM) modified in the molecular beacon was measured to analyze the amount of produced anti-sense RNA.

As a result, as illustrated in FIG. 2, it was confirmed that the NESBA method of the present invention exhibited remarkably high anti-sense RNA amplification efficiency in an experiment for detecting target RNA (H3N2 influenza virus gRNA, 800 fM) at the same concentration compared with an existing NASBA reaction.

Example 2. Verification of Sensitivity of Nicking/Extension-Chain-Reaction-System-based Isothermal Nucleic Acid Amplification Technique Using Nicking Enzyme and DNA Polymerase Activity Analysis samples (20 μL) containing a target RNA at various concentrations (0.1 pM, 0.2 pM, 0.5 pM, 0.8 pM, 8 pM, and 80 pM) were prepared in the same manner as in Example 1, and then a NESBA reaction was performed to analyze sensitivity to the target RNA. More specifically, after the NESBA reaction, an experiment was performed using an Infinite M200 PRO (Tecan) to measure a fluorescence signal generated from a fluorescein modified in the molecular beacon. In addition, a device for measuring the fluorescence signal generated from fluorescein was set as follows, but the present invention is not limited thereto.

Excitation wavelength: 480 nm
Emission wavelength: 520-600 nm

Figure 3:
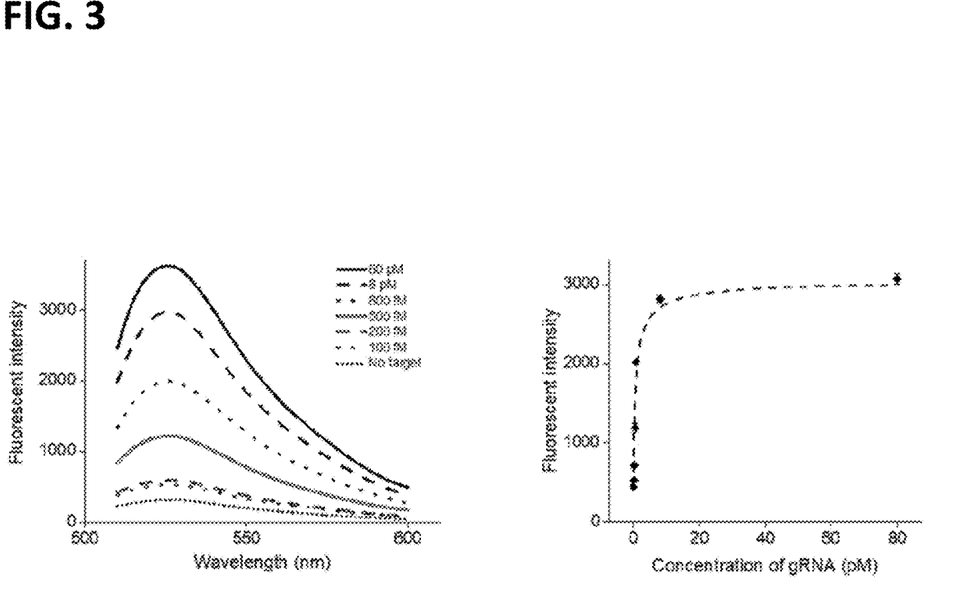
FIG. 3 illustrates the results of confirming target RNA detection sensitivity of NESBA of the present invention.

As a result, as illustrated in FIG. 3, it was confirmed that the limit of detection (LOD) of the target RNA of the NESBA technique was 0.72 fM.

Figure 4:
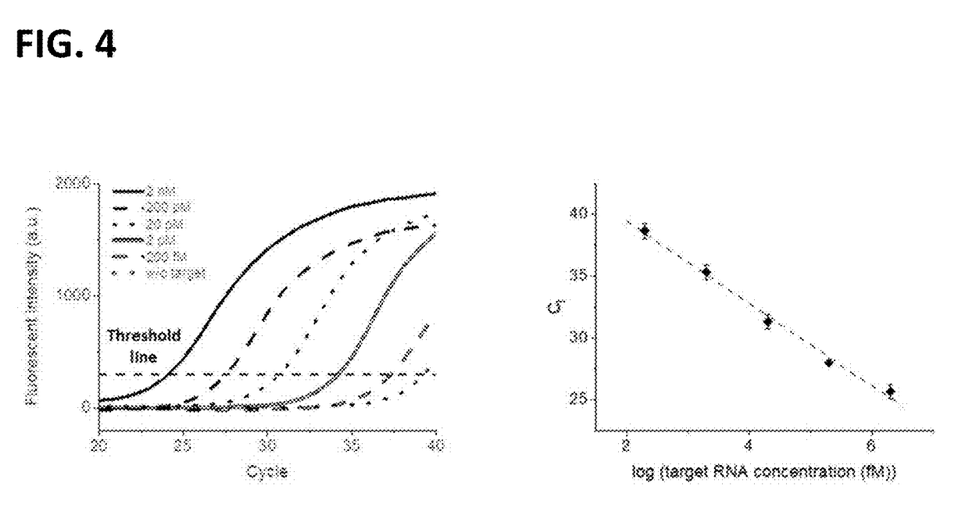
FIG. 4 illustrates the results of confirming target RNA detection sensitivity using reverse transcription PCR.

Example 3. Verification of Practicability of Nicking/Extension-Chain-Reaction-System-Based Isothermal Nucleic Acid Amplification Technique Using Nicking Enzyme and DNA Polymerase Activity To verify the practicability of the NESBA technique of the present invention, an experiment for detecting a target RNA using a commercialized reverse transcription PCR kit was carried out, and the results were compared with the performance of a NESBA technique. In the practicability verification experiment of the present example, a TOPreal™ One-step RT qPCR kit (Enzynomics co Ltd.) was used, and the target RNA detection experiment was performed according to an experimental method provided by the above product. As a result of performing an experiment for detecting a target RNA at various concentrations (0.2 pM, 2 pM, 20 pM, 200 pM, and 2000 pM) by using the reverse transcription PCR kit, it was confirmed that the reverse transcription PCR technique exhibited a limit of detection of the target RNA of 0.52 fM (see FIG. 4), and from these results, it was confirmed that the NESBA technique of the present invention, which does not use expensive reverse transcription equipment, exhibited detection performance comparable to that of an existing reverse transcription PCR technique.

INDUSTRIAL APPLICABILITY

A target RNA detection method using NESBA according to the present invention does not require a temperature control reaction, as is required in an existing reverse transcription PCR technique, and thus can be used as a technique for on-site diagnosis, not only as a technique used in specialized diagnostic centers and large hospitals, can realize enhanced amplification efficiency compared to an existing NASBA reaction, and can address false signal problems that may occur in a target RNA detection process.

While specific embodiments of the present invention have been described in detail, it will be obvious to those of ordinary skill in the art that these detailed descriptions are merely exemplary embodiments and are not intended to limit the scope of the present invention. Therefore, the substantial scope of the present invention should be defined by the appended claims and equivalents thereto.

Sequence List Free Text
    Electronic files attached

---

The invention claimed is:

1. A method of detecting a target RNA based on a nicking/extension chain reaction system, the method comprising:
 (a) hybridizing a target RNA with a first primer comprising a sequence complementary to the target RNA, a T7 promoter sequence, and a second DNA nicking enzyme recognition nucleotide sequence, and then producing complementary DNA of the target RNA using a reverse transcriptase;
 (b) degrading the target RNA bound to the complementary DNA produced in step (a) by a ribonuclease;
 (c) hybridizing the complementary DNA with a second primer comprising a sequence complementary to the complementary DNA and a DNA nicking enzyme recognition nucleotide sequence, and then producing a double-stranded DNA comprising a T7 promoter and the first and second enzyme recognition nucleotide sequences using a reverse transcriptase;
 (d) treating the double-stranded DNA produced in step (c) with a DNA nicking enzyme to cleave the DNA nicking enzyme recognition sites of the double-stranded DNA, and then amplifying the T7-promoter-containing double-stranded DNA using DNA polymerase; and
 (e) producing an anti-sense RNA from the T7-promoter-containing double-stranded DNA amplified in step (d) using T7 RNA polymerase, and then detecting the produced anti-sense RNA.

2. The method according to claim 1, wherein steps (a) to (e) are performed at isothermal temperature.

3. The method according to claim 2, wherein the isothermal temperature is in a range of 40° C. to 42° C.

4. The method according to claim 1, wherein the ribonuclease is an enzyme that that selectively degrades only RNA in a DNA/RNA hybrid.

5. The method according to claim 1, wherein the DNA polymerase is an enzyme having strand displacement activity on DNA bound to a template.

* * * * *

UNITED STATES PATENT AND TRADEMARK OFFICE
CERTIFICATE OF CORRECTION

PATENT NO. : 11,466,312 B2
APPLICATION NO. : 16/958683
DATED : October 11, 2022
INVENTOR(S) : Hyun Gyu Park It is certified that error appears in the above-identified patent and that said Letters Patent is hereby corrected as shown below:

In the Claims

Column 13, Line 21, Claim 1, "a second DNA nicking enzyme" should be -- a first DNA nicking enzyme --.

Column 13, Line 29, Claim 1, "a DNA nicking enzyme" should be -- a second DNA nicking enzyme --.

Signed and Sealed this
Twentieth Day of December, 2022

Katherine Kelly Vidal
*Director of the United States Patent and Trademark Office*